United States Patent [19]
Pomerantzeff

[11] 3,954,329
[45] May 4, 1976

[54] WIDE-ANGLE OPTHALMOSCOPE EMPLOYING TRANSILLUMINATION

[75] Inventor: Oleg Pomerantzeff, Brookline, Mass.

[73] Assignee: Retina Foundation, Boston, Mass.

[22] Filed: Dec. 27, 1974

[21] Appl. No.: 536,879

Related U.S. Application Data

[63] Continuation-in-part of Ser. Nos. 292,150, Sept. 25, 1972, and Ser. No. 512,327, Oct. 4, 1974.

[52] U.S. Cl. ............................. 351/16; 350/96 B; 351/6; 351/7
[51] Int. Cl.² ...................... A61B 3/14; A61B 3/10; A61B 3/12
[58] Field of Search .................. 350/96 B; 351/6, 7, 351/16; 128/2 T

[56] References Cited
UNITED STATES PATENTS

3,630,602  12/1971  Herbert ............................. 351/16
3,770,342  11/1973  Dudragne ........................ 351/16 X

*Primary Examiner*—Paul A. Sacher
*Attorney, Agent, or Firm*—Kenway & Jenney

[57] ABSTRACT

Apparatus for viewing an eye fundus through a contact lens has a lamp element that illuminates the fundus through the sclera. The lamp element preferably includes at least one fiber optic bundle with an exit facet for placement contiguous with the sclera, generally through whatever thickness of ocular conjunctiva is present. The apparatus can include a further lamp element having fiber facets arrayed around the viewing lens for illuminating the fundus through the crystal lens of the eye being examined.

12 Claims, 3 Drawing Figures

U.S. Patent  May 4, 1976  3,954,329
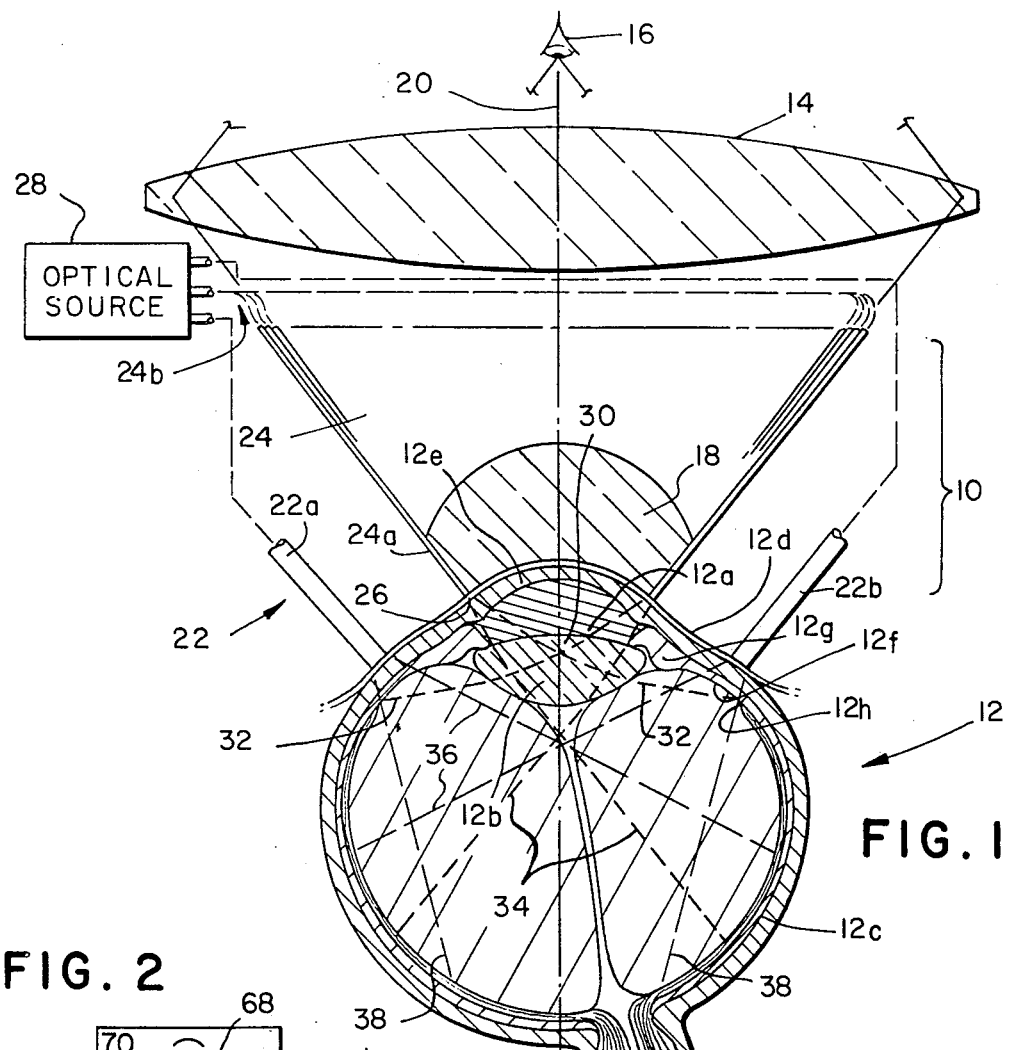
FIG. 1
FIG. 2
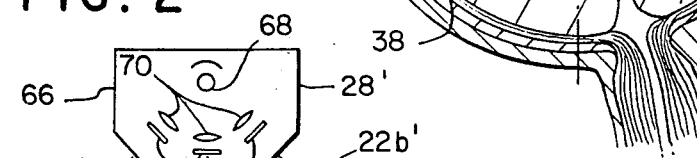
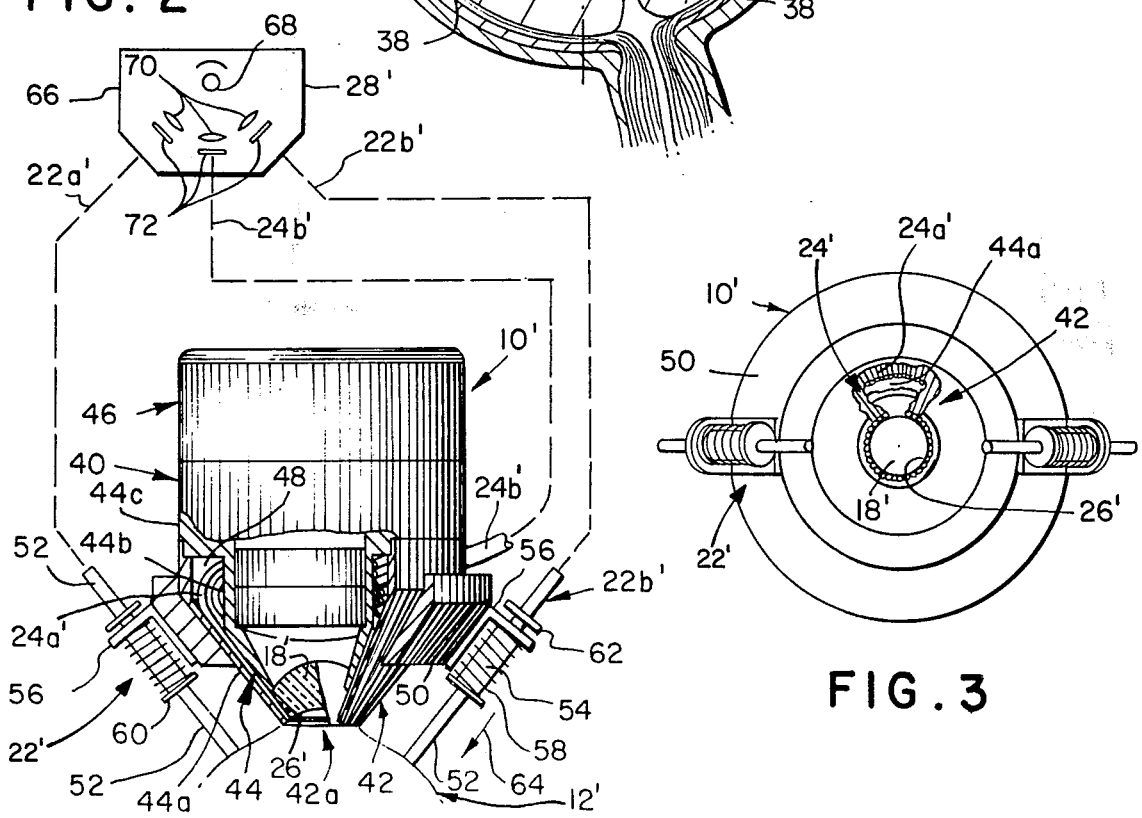
FIG. 3

WIDE-ANGLE OPTHALMOSCOPE EMPLOYING TRANSILLUMINATION

CROSS REFERENCE TO RELATED APPLICATIONS

This application is a continuation-in-part of my co-pending application Ser. No. 292,150 filed Sept. 25, 1972 entitled "Wide-Angle Ophthalmoscope", and my co-pending application Ser. No. 512,327 filed Oct. 4, 1974 entitled "Wide-Angle Ophthalmoscope and Fundus Camera", both of which are assigned to the assignee hereof.

BACKGROUND OF THE INVENTION

This invention relates to an ophthalmoscope, i.e. an instrument for viewing the interior of the eye. More particularly, the invention provides an ophthalmoscope having a new lamp element that illuminates the eye fundus in a manner that minimizes interference with the viewing of the fundus through the crystalline lens of the eye.

The invention thus provides a new wide-angle ophthalmoscope having a superior field of view and a superior observable field as compared with prior devices of this kind. The field of view is the area of the fundus covered by the viewer, or viewing instrument, in any direction of observation in a single image; and the observable field is the area of the fundus beyond which the ophthalmoscope is unable to reach. The invention also provides an improvement in the control, and consequently in the uniformity, of the illumination over the fundus.

Due to these and other advantages set forth below, an ophthalmoscope embodying the invention enables superior viewing of the entire retina, and photographing it, in a single image. The ophthalmoscope in addition requires significantly less dilation of the patient's pupil than prior wide-angle ophthalmoscopes. This enables ophthalmologic examination in situations where it previously was not possible due to restrictions on the allowable dilation, as is the case with patients suffering from diabetes.

The co-pending applications noted above describe wide-angle ophthalmoscopes having improved constructions for both illumination and viewing exclusively through the crystal lens of the patient, i.e. of the eye being observed. However, these prior wide-angle ophthalmoscopes require precise construction and precise placement on the patient's eye, as well as significant dilation of the patient's pupil. Also, there is often a noticeable diminution of illumination at the periphery of the fundus.

Accordingly, it is an object of this invention to provide an optical, fundus-viewing instrument in which the lamp element imposes less constraint on the viewing lens than in prior devices of this kind.

It is also an object of the invention to provide a wide-angle fundus-viewing instrument having a lamp element that provides control over the illumination of the fundus and particularly which illuminates the fundus with high uniformity.

A further object of the invention is to provide a wide-angle ophthalmoscope that requires relatively small dilation of the pupil of the eye being examined.

Another object of the invention is to provide an ophthalmologic device of the above character which requires less precision and hence less cost to fabricate than comparable prior devices and which is relatively easy to use.

It is also an object of the invention to provide an ophthalmologic device of the above character having no or fewer lamp elements according to the desired illumination, which direct illumination through the lens of the patient's eye.

Other objects of the invention will in part be obvious and will in part appear hereinafter.

BRIEF DESCRIPTION OF DRAWINGS

For a fuller understanding of the nature and objects of the invention, reference should be made to the following detailed description and the accompanying drawings, in which:

FIG. 1 is a schematic, horizontal plan view, largely in section, of an ophthalmoscope embodying the invention operatively positioned on an eye;

FIG. 2 is a plan view, partly in section, of a preferred construction for the ophthalmoscope of FIG. 1; and FIG. 3 is a frontal elevation view of the ophthalmoscope of FIG. 2.

SUMMARY OF THE INVENTION

The invention stems from the finding that the illumination of a retina for ophthamologic examination can successfully be done through the sclera. This is in contrast to illumination exclusively through the crystal lens of the eye being examined, as previously done. In the new instrument, the sclera diffuses the light which spreads it over the entire fundus, as desired. As a result, a lamp element can introduce illumination at as few as a single restricted location. This is in contrast to the prior practice which generally required a distributed lamp construction for projecting a uniform pattern of light.

With the so-called transillumination through the sclera which the invention provides, the viewing lens of the ophthalmologic device can be optimized to a greater extent than previously to provide a large field of view and a large observable field. This is because the lamp elements previously required at the crystalline lens, where the viewing lens must be located, can be illuminated, or at least diminished. In either case, there is significantly more freedom to employ the desired viewing lens construction.

The transillumination is preferably directed through a narrow region of the sclera, termed the pars plana. This region lies in a generally annular area between the ciliary body and the ora cerrata. The optical transmission of light applied to the pars plana, to the interior of the eye, exceeds 50%. Elsewhere on the sclera the optical transmittance is significantly less.

Examination of an eye with transillumination through the pars plana and with a correspondingly optimized viewing lens can provide a field of view and an observable field of 160°, all of which is illuminated with relatively high uniformity. Hence, this field can be both examined by an observer and photographed or otherwise recorded as a single image.

The invention accordingly comprises the features of construction, combination of elements, and arrangement of parts exemplified in the constructions hereinafter set forth, and the scope of the invention is indicated in the claims.

DESCRIPTION OF ILLUSTRATED EMBODIMENT

FIG. 1 shows a wide-angle ophthalmoscope 10 according to the invention operatively disposed contacting a human eye indicated generally at 12. The ophthalmoscope is in optical alignment with a field lens system 14 in front of a viewing or recording device 16, which can include an observer's eye, a camera, or other optical viewing or recording equipment. The ophthalmoscope has a contact lens 18 that images the eye fundus outside the eye. That is, the contact lens 18 enables an exterior viewer to observe up to essentially a 160° solid angle of the eye fundus through the pupil 12a and crystalline lens 12b of the eye. The field lens system 14 focuses this image of the fundus on the instrument 16.

The ophthalmoscope 10 has a lamp element 22, illustrated in the form of a bundle 22a of optical fibers, which directs light from a source 28 into the interior of the eyeball through the sclera 12c, and whatever thickness of the conjunctiva 12d which is present. The sclera and adjacent layers of the eye structure diffuse the light which the lamp element 22 projects. Hence, the resultant illumination within the eyeball is scattered substantially throughout the fundus. This is advantageous, for it allows the placement of the bundle 22a on the sclera, as well as the construction of the bundle itself, to be significantly less exacting than is the case with prior illuminators for wide-angle ophthalmoscopes. The diffusion within the eyeball of the light directed onto the sclera also makes it possible for a confined bundle 22a to illuminate the fundus, in contrast to requiring a symmetrical distributed array of illuminating elements as previously required. Thus, a single bundle 22a suffices for many ophthalmologic examinations.

However, FIG. 1 shows a preferred construction of the lamp element 22 in which there is a second bundle 22b constructed identically to the bundle 22a and located on the other side of the lens 18, as shown. The two bundles 22a and 22b preferably are disposed on the horizontal sides of the pupil in the access space normally available on an eye, i.e. the placement of one is temporal and of the other is nasal. Where desired, of course, one or more bundles can be placed elsewhere on the eyeball. However, bundles located vertically above and/or below the pupil generally require displacement of the eyelid.

With further reference to FIG. 1, the illustrated ophthalmoscope 10 includes a second lamp element 24 formed by optical fibers disposed in a conical array contiguously around the contact lens 18, in the manner disclosed in the prior patent applications noted above. The facets of the conically-arrayed fibers 24a form a ring 26 which contacts the eye cornea 12e contiguously circumferential to the contact by lens 18. The illumination of the fundus which the fibers 24a project increases the overall level of illumination. Further, it often is desirable because it provides more uniform illumination throughout the fundus and illumination over a larger portion of the fundus. In particular, the illustrated lamp element 24 generally extends and increases the illumination in the peripheral portion of the fundus, which appears forward of the eye 12 or upward in FIG. 1. However, as indicated, the lamp element 24 can be omitted depending on factors such as the illumination desired within the eyeball, the design requirements of the lens 18, and the design and performance of the first lamp element 22.

In view of the foregoing, it should be understood that when in use, the ophthalmoscope 10 is centered on the eye 12 and hence the lens 18 and the illuminating ring 26 of the lamp element 24 both are located on the cornea 12e optically aligned with the lens 12b along the axis 20. Each bundle 22a, 22b of the lamp element 22 is generally normal to the eyeball and is disposed at the sclera 12c. Further, each bundle is located at the pars plana 12f, which is the annular portion of the sclera between the ciliary body 12g and the ora cerrata 12h. As previously noted, the optical transmission of the sclera and the adjacent layers at the ora cerrata is relatively high, due to the small thickness of optically-absorbing material there, as contrasted with adjacent regions.

The above-referenced prior applications, and the article "Design of a Wide-Angle Ophthalmoscope", by O. Pomerantzeff et al, *Arch. Ophthal.* Vol 86, pages 420–424, October 1971, set forth that the illumination of the fundus through the crystalline lens 12b, i.e. by the lamp element 24, should not enter this lens at the entrance pupil 30 of the viewing system. (This entrance pupil extends over the area of the lens 12b surface through which the fundus is viewed by means of the contact lens 18.) Otherwise, reflections of the incident illumination enter the viewing system and degrade the observed image. To keep the entrance pupil 30 free of incident illumination, and to enable the contact lens 18 to image the entire fundus, the illuminating ring 26 of fiber facets is radially spaced from the central axis 20 and is angled as shown. In particular, the illustrated ophthalmoscope 10 is constructed with a five millimeter radius of the ring 26 from axis 20, and with the fibers 24a at a 39° angle from this axis. The illuminating fibers 24a extend from the ring 26 normal to the ring-forming facets. From this initial normal and straight-line configuration, the fibers can, where desired, be bent further away from the central axis 20. This is indicated with the illustrated configuration, where, beyond the lens 18, the fibers 24a are gathered into a single bundle 24b that feeds to the optical source 28.

With this configuration, the lamp element 24 directs illumination to the eye with the extreme anterior ray 32 from each point along the ring 26 passing outside the periphery of the entrance pupil 30, and not within it. Notwithstanding the foregoing limitation, the anterior ray 32 can illuminate the periphery of at least a 150° field.

The lamp element 24 typically is constructed with commercially available fibers having a diameter of 20 microns and having a numerical aperture of 0.55, which results in an angular aperture of 66° in air and of 48° within the eye. With fibers projecting such an aperture and oriented as above, the extreme posterior ray 34 from each point on the ring 26 extends deeply into the eyeball, as FIG. 1 also shows.

Thus, the illustrated lamp element 24 illuminates the periphery and side of the fundus. Only the generally circular, central, posterior fundus area bounded by the rays 34, 34 does not receive direct illumination from this lamp element.

The ophthalmoscope contact lens 18 functions, when in contact with an eye cornea, to increase the power of the optical system of the eye being examined and to bring the image of the fundus from infinity to a finite distance in front of the eye. For this purpose, the lens has a concavo-convex configuration with generally frusto-conical sides. The illustrated lens has a high refractive index ($n_d$), e.g. of 2.1, a concave inner surface having a radius of curvature of 8.2 millimeters, and a convex outer surface having a radius of curvature of 10.2 millimeters. This construction results in the lens having a thickness along the axis 20 of 9.2 millimeters. The frusto-conical sides of the lens are angled at 39° relative to the axis 20, i.e. it fills the 78° solid angle formed within the concial configuration of the lamp fibers 24a. The lens 18 suitably is constructed of an optical glass such as is available from the Eastman Kodak Company under its designation EK 911.

Turning to the fiber optic bundles of the lamp element 22, as already noted each is configured to be disposed on the eye to illuminate the fundus through the sclera at the region of maximum optical transparency, i.e. at the pars plana. There preferably are two bundles 22a and 22b as illustrated, one located temporally and the other in a nasal location. Each bundle contacts the sclera at a spacing generally between 11 and 17 millimeters from the axis 20 in order to engage the pars plana. The exact location of the bundles against the eyeball for optimum illumination will, of course, vary depending on the size of the eyeball being examined. A construction in which each bundle has a diameter of 5 millimeters at its engagement with the eyeball, and in which the bundle engages the eyeball at around 14 millimeters from the central axis 20, suffices for most instances. Each bundle can be constructed with fibers having the same characteristics as those described above for use in the lamp element 24.

FIG. 1 shows that the resultant 48° angular aperture of direct illumination, i.e. excluding diffusion and scattering, from each bundle 22a and 22b is within a solid angle bounded by the rays 36 and 38. However, as noted, there is significant diffusion of the illumination from the lamp 22 in passing into the interior of the eyeball so that the illumination from each bundle is scattered far beyond the region of direct illumination. This scattering generally is considered desirable, for it results in illumination of the entire observable field of the fundus by the lamp element 22 itself, i.e. without additional illumination as from lamp element 24.

A further and significant advantage of the ophthalmoscope 10 is that it can be used without requiring full dilation of the pupil of the eye being examined. In fact, whereas dilation to 7 or 8 millimeters is required with prior wide-angle ophthalmoscopes, the present instrument provides a full-fundus field in a single image with dilation to only approximately 3 millimeters. The reason for this improvement is that, with illumination of the fundus through the sclera, it is no longer necessary to introduce through the crystalline lens 12b illumination to cover the entire fundus.

FIGS. 2 and 3 show a construction of the ophthalmoscope of FIG. 1 in which each bundle 22a and 22b of the lamp element 22 is mounted for placement with the contact lens 18 but is supported for essentially independent contact with the eye. The construction also includes the lamp element 24 of FIG. 1. Elements of the FIG. 1 ophthalmoscope 10 which are shown in the construction of FIGS. 2 and 3 bear the same reference numeral as in FIG. 1 but with a prime; thus FIGS. 2 and 3 show a construction for an ophthalmoscope 10'. The ophthalmoscope 10' has a housing 40 that includes a hollow conical member 42 and ring members 44 and 46; these members, which interfit to form a single assemblage, are optically opaque and of rigid structural material, typically of aluminum or stainless steel. The fibers 24a' of lamp element 24' are disposed in a conical array between a conical wall of member 42 and the corresponding outer surface of the lens 18'. An adhesive of the kind conventionally used for fixing optical fibers in place preferably fills the interstices between the lens 18', the fiber 24a', and this wall of the member 42 to secure the assembly of these elements. The lens 18' and the ring 26' of the optical fibers are centered at an apex aperture 42a of the conical member.

The illustrated ring member 44 is composed of a concentric axial succession of apertured hollow elements namely a conical element 44a, a cylindrical element 44b and a further cylindrical element 44c joined by a radial wall to the element 44b. As shown in FIG. 2, this member 44 seatingly engages, with the edge of the aperture, the periphery of the concave outer surface of lens 18' to clamp the lens in place against the conical member 42 with the fibers 24a' sandwiched therebetween. The ends of the fibers as noted lie between the lens 18' and the conical member 42; from there the fibers extend between the conical walls of members 42 and 44 to an annular passage 48 formed between the cylindrical element 44b and a cylindrical rim of the conical member 42. Within this passage, there is a transition of the fibers 24a' from the conical configuration to a single, densely packed bundle 24b' that extends outward through an aperture in the housing 40 and, within conventional cladding, to the optical source 28'.

The cylindrical element 44b of the ring member 44 and the ring member 46 mount optical elements of the field lens system 14'. The above-noted application Ser. No. 512,327 discloses the construction of the housing members 42, 44 and 46, and the design of a preferred lens system 14; that disclosure is incorporated herein by reference.

With continued reference to FIGS. 2 and 3, the transilluminating lamp element 22' includes a bundle-supporting collar 50 seated on the housing 40 and carrying the two optical fiber bundles 22a' and 22b'. Each bundle is slidingly mounted and spring biased to engage and lightly bear against the eyeball independent of the other and independent of the engagement of the contact lens 18' with the cornea. More particularly, the fibers of each bundle 22a' and 22b' are clad within a rigid self-supporting tube 52. Each tube 52 is seated on bearings within a sleeve 54 that is affixed by a bracket to the collar 50. The sleeve-carried bearings thus mount the tube-encased bundle for sliding motion along the bundle axis with minimal friction. A coil spring 58 urges the bundle forward, i.e. toward the bottom in FIG. 2, relative to the collar 50. The spring is compressed between the sleeve-mounting bracket 56 and a stop flange 60 secured to each tube 52, as shown. A further stop flange 62 affixed to each tube rearward of its engagement with the sleeve and bracket limits the forward motion of each bundle due to the compression spring 58, i.e. when the ophthalmoscope 10' is not in use so that the bundles are not engaged against an eye.

With this construction and as shown in FIG. 2, when the ophthalmoscope 10' is operatively positioned against an eye, the bundles 22a' and 22b' engage the sclera at the pars plana first, i.e. before the contact lens 18' and the illuminating ring 26' engage the cornea. Further movement of the ophthalmoscope toward the eye pushes the bundles back against the small force of the coil springs 58, i.e. against the spring forces designated with arrow 64, unitl the fiber ring and contact lens are seated on the cornea, which is the condition shown in FIG. 2.

FIG. 2 also shows that the optical source 28' typically is constructed with a housing 66 that contains a bulb 68 and three lenses 70, each of which focuses light from the bulb 68 onto the input facet of the three illuminating fiber optic bundles 22a', 22b' and 24b'. A separate optical filter 72 typically is inserted in each optical path between the bulb 68 and the bundle input facets. Each filter typically is selected to pass the selected optical wavelengths appropriate for the desired fundus illumination of the eye being examined.

For clarity of description the invention has been described in terms of an ophthalmoscope. As noted above, this term is used herein with reference to any device for examining (including recording) an eye fundus. Hence the device 10 illustrated and described herein can be part of a fundus camera, or of another instrument which is used for viewing, recording or otherwise examining an eye fundus.

It will thus be seen that the objects set forth above, among those made apparent from the preceding description, are efficiently attained. Since certain changes may be made in the above construction without departing from the scope of the invention, it is intended that all matter contained in the above description or shown in the accompanying drawings be interpreted as illustrative and not in a limiting sense.

It is also to be understood that the following claims are intended to cover all the generic and specific features of the invention herein described, and all statements of the scope of the invention, which, as a matter of language, might be said to fall therebetween.

Having described the invention, what is claimed as new and secured by Letters Patent is:

1. In a device for examining an eye fundus under applied illumination, said device having lamp means for illuminating the fundus and a contact lens for viewing the fundus, the improvement in which said lamp means comprises means for directing light onto the sclera of the eye being examined for transmission through the sclera to illuminate the fundus.

2. In a device according to claim 1, the further improvement comprising means for positioning said light-directing means at the pars plana.

3. In a device according to claim 1, the further improvement wherein said light-directing means includes a fiber optic bundle having an exit facet for placement on the eye at a scleric region having relatively high optical transmission from outside the eye to the fundus.

4. In a device according to claim 1, the further improvement wherein said light-directing means includes first and second fiber optic bundles, each of which has an exit facet for placement on an exterior surface of the eye at a region of the sclera having relatively high optical transmission to the eye fundus.

5. In a device according to claim 3, the further improvement comprising mounting means supportingly mounting said bundle with said contact lens, and including adjustable positioning means for accommodating movement of said bundle relative to said lens resultant from eye contact.

6. An ophthalmoscope for examining an eye, said ophthalmoscope comprising
  A. a lens for forming an anterior image of the eye fundus,
  b. a fundus-illuminating lamp element for directing light onto the sclera of the eye for illumination therethrough of the eye fundus, and
  C. support means mounting said lens and said lamp element, said support means mounting said lens for disposition in optical alignment with an entrance pupil on the crystalline lens of the eye being examined and mounting said lamp element for directing fundus-illuminating light onto the eye sclera with essentially no light being directed therefrom onto such entrance pupil.

7. An ophthalmoscope as defined in claim 6
  A. wherein said lens includes a contact lens for placement on the eye cornea,
  B. wherein said lamp element includes a fiber optic bundle having an exit facet for placement on the eye sclera, and
  C. wherein said support means includes spring means for accommodating movement of said fiber bundle relative to said contact lens such that said bundle can engage the eye independent of engagement of said contact lens with the eye.

8. An ophthalmoscope as defined in claim 6
  A. in which said lamp element includes a bundle of optical fibers having an exit facet,
  B. in which said support means mounts said bundle laterally spaced from said lens for engaging the exit facet of said bundle against the eye sclera and for concurrently disposing said lens in such optical alignment with the eye lens.

9. An ophthalmoscope as defined in claim 8
  A. in which said lens includes a contact lens for disposition contiguous with the eye cornea in such optical alignment, and
  B. said support means includes positioning means for engaging the exit facet of said bundle contiguous with the eye sclera when said contact lens is contiguous with the eye cornea.

10. An ophthalmoscope as defined in claim 8 in which said support means mounts said bundle for engagement of said facet thereof with the eye sclera at the pars plana.

11. An ophthalmoscope as defined in claim 7 comprising a further lamp element having an array of optical fibers disposed peripherally about said lens for directing light onto the fundus of the eye through the lens thereof outside such entrance pupil.

12. An opthalmoscope as defined in claim 11 further comprising an optical source introducing light into the optical fibers of each said lamp element, said source including optical filter means for introducing said light into each said lamp element with independently selectable spectral wavelengths.

* * * * *

UNITED STATES PATENT AND TRADEMARK OFFICE
CERTIFICATE OF CORRECTION

PATENT NO. : 3,954,329
DATED : May 4, 1976
INVENTOR(S) : Oleg Pomerantzeff

It is certified that error appears in the above-identified patent and that said Letters Patent are hereby corrected as shown below:

Column 5, line 23, before "the eyeball", the word is --against--.

Column 6, line 6, change "fiber" to --fibers--.

Column 8, line 7, change "b." to --B.--.

Signed and Sealed this

Twenty-sixth Day of October 1976

[SEAL]

Attest:

RUTH C. MASON
Attesting Officer

C. MARSHALL DANN
Commissioner of Patents and Trademarks